United States Patent [19]

Veracini

[11] Patent Number: 4,504,689
[45] Date of Patent: Mar. 12, 1985

[54] PROCESS FOR THE PREPARATION OF PHENATES SUBSTITUTED BY HALOGEN GROUPS OR OF THE CORRESPONDING PHENOLS

[76] Inventor: Serge Veracini, 36 Avenue de Ménival, 69005, Lyon, France

[21] Appl. No.: 509,062

[22] Filed: Jun. 29, 1983

[30] Foreign Application Priority Data

Jun. 29, 1983 [FR] France .................................. 82 11616

[51] Int. Cl.$^3$ .............................................. C07C 39/24
[52] U.S. Cl. .................................. 568/778; 568/739; 568/775; 568/777; 568/796
[58] Field of Search ............... 568/774, 775, 778, 777, 568/739, 796

[56] References Cited

U.S. PATENT DOCUMENTS 3,481,991 12/1969 Cohen ................................... 568/775
3,651,154 3/1972 Klingsberg ........................... 568/737
4,122,288 10/1978 Christensen et al. ............... 568/775
4,225,731 9/1980 Marhold et al. ..................... 568/775
4,259,510 3/1981 Johnson ................................ 568/775
4,262,152 4/1981 Johnson ................................ 568/775

FOREIGN PATENT DOCUMENTS 2042569 3/1972 Fed. Rep. of Germany ...... 568/774
1408502 7/1965 France ................................. 568/775
1110232 4/1968 United Kingdom ................ 568/775

Primary Examiner—Werren B. Lone
Attorney, Agent, or Firm—Morgan, Finnegan, Pine, Foley & Lee

[57] ABSTRACT

This invention relates to a process for preparing phenates substituted by halogen groups of the corresponding phenols which comprises reacting a halo-substituted benzene with a powdered base having a particle size of less than 4 mm in the presence of an aprotic polar solvent.

19 Claims, No Drawings

PROCESS FOR THE PREPARATION OF PHENATES SUBSTITUTED BY HALOGEN GROUPS OR OF THE CORRESPONDING PHENOLS

This invention relates to a process for preparing phenates and phenols which are substituted by halogen groups.

More particularly, this invention relates to the preparation of phenols and phenates of the formula:

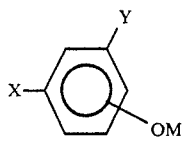
(I)

wherein
- X is selected from the group consisting of halogen and trifluoromethyl;
- Y is selected from the group consisting of hydrogen, halogen, trifluoromethyl and alkyl having from 1 to 4 carbon atoms, provided that when Y is halogen, X is trifluoromethyl; and
- M is selected from the group consisting of hydrogen, alkali metal ion or alkaline earth metal ion.

BACKGROUND OF THE INVENTION

European patent application No. 19,388 describes a process for preparing the above phenates and phenols from a compound having the formula:

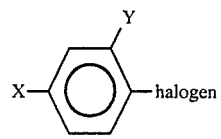
(II)

in which X and Y have the meanings given above. The process disclosed in European patent application No. 19,388 consists of reacting a compound of the formula (II) with an alkali metal or alkaline earth metal hydroxide in a binary solvent system requiring both an aprotic polar solvent having a dielectric constant of about 30 to 70 and a non-nucleophilic hydroxylated solvent. For example, the cosolvents must be present in the reaction at a ratio in the range of about 1 to 30 parts non-nucleophilic hydroxylated cosolvent to about 100 parts of the polar, aprotic solvent.

The process described in European patent application No. 19,388 process is relatively time-consuming and somewhat complex, as it requires at least two solvents.

It is, therefore, one object of this invention to provide a process for preparing phenates and phenols of formula (I) having a significantly simpler solvent system.

Another object of this invention is to provide a process for preparing phenates and phenols which is not time-consuming.

It is still another object of this invention to provide a process giving high yields of compounds having formula (I).

Still another object of this invention is to provide a process which is highly selective for the desired products.

BRIEF SUMMARY OF THE INVENTION

It has now been found that these objects can be achieved by virtue of the novel process of this invention.

This process comprises reacting a compound having the formula:

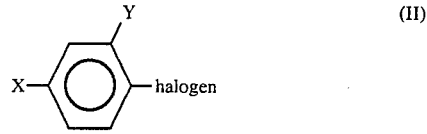
(II)

with a powdered basic compound component selected from the group consisting of alkaline earth and alkali metal hydroxides, in the presence of an aprotic polar solvent, said hydroxide having a particle size of less than 4 mm.

DETAILED DESCRIPTION OF THE PREFERRED EMBODIMENTS

The process of this invention is preferably performed at a temperature between about 50° and 120° C. More preferably, the reaction should take place at a temperature between about 60° and about 90° C. The process of this invention is preferably carried out at atmospheric pressure.

The powdered basic hydroxide compounds are preferably alkaline earth metal hydroxides and alkali metal hydroxides. More preferably, calcium hydroxide, magnesium hydroxide, sodium hydroxide and potassium hydroxide should be used. Most preferable are sodium and potassium hydroxides. A mixture of hydroxides may be used as the basic compound component in the reacton. The molar ratio of powdered basic compound to the starting reagent of Formula (II) is preferably about 1 to 4. Most preferably, the molar ratio is about 2 to 3.

The hydroxide component used in this invention is preferably powdered and available for use in particle form. It is thought that powdering renders the reaction more effective and efficient. While the hydroxide particles are of varying size, their size should be less than 4 mm in diameter. Preferably the size of the particles of the powdered component should be in the range of about 0.005 mm to about 4 mm. More preferably, the size should be in the range of about 0.005 mm to about 2 mm and most preferably, between about 0.005 mm and about 1.5 mm. Particle size is determined by running the powdered hydroxide through a calibrated sieve.

The aprotic polar solvents used in the novel process of this invention should have a dielectric constant between about 30 and about 70. Preferably, aprotic polar solvents which can be used include hexamethylphosphotriamide, dimethylacetamide and dimethyl sulphoxide and N-methylpyrrolidone. Most preferable are dimethyl sulphoxide and dimethylacetamide.

It is preferable that one aprotic polar solvent be used in the process of this invention. However, more than one aprotic polar solvent may be emloyed. The aprotic polar solvent is believed to aid in solubilizing the hydroxide base, in solubilizing the phenate reaction product and in making the reaction medium more homogeneous. In addition, it is thought that the aprotic polar solvent promotes the aromatic nucleophilic substitution reaction which takes place during the process of this invention.

The process according to the invention may be carried out in the presence of a catalyst. Catalysts that can be used in the process of this invention include quaternary ammonium salts. Such salts include, for example, monoalkyl ammonium, dialkylammonium and trialkylammonium salts. Other catalysts which can be used are crown ethers and trispolyoxyalkylamines, especially when containing from 6 to 40 carbon atoms. Such catalysts are described in European Pat. No. 21,927, which is hereby incorporated by reference. Such a catalyst may be present in an amount of between about 1 and about 20% of the molar amount of hydroxide component present in the reaction mixture.

The reaction should, preferably, take place in an inert atmosphere in order to avoid the oxidation of the phenate reaction products. Any inert atmosphere, for example argon or nitrogen, may be used.

The predominant in situ reaction product of the novel process of this invention is a phenate salt according to formula II. The phenol is obtained by neutralization of the salt with an aqueous solution of an acid. Any unreacted starting materials may be recovered by methods known in the art, e.g. distillation.

Both the phenol and the phenate can be used as an intermediate in the synthesis of diphenyl ether compounds and phenoxybenzoic acid derivatives which are known to be useful as herbicides. No further purification steps are necessary after obtaining the phenate or phenol reaction products in order to use them as intermediates.

The examples which follow, which in no way limit the invention, illustrate the invention and show how it can be carried out.

The "degree of conversion" is based upon the starting compound of Formula II. Thus degree of conversion is the percentage of the molar amount of starting compound of Formula II used or consumed in the reaction divided by the molar amount of that compound at the start of the reaction. The "yield" is defined as:

$$100 \times \frac{\text{Number of moles of reaction product of Formula I produced during the process}}{\text{Number of moles of the starting compound Formula II which were used or consumed during the process}}$$

EXAMPLE 1

A mixture of 3,4-dichlorotrifluoromethylbenzene (30 millimols) and powdered NaOH (70 millimols), prepared from sodium hydroxide pellets, containing 98.5% by weight of sodium hydroxide, ground in a mechanical mill and sieved so as to give a particle size of between 50 and 300 microns, is reacted in dimethyl sulphoxide (28 ml) for 7 hours at 80° C. The mixture is stirred using a stirrer rotating at a speed of 400 rpm, and kept under an inert argon atmosphere.

At the end of the reaction, the reaction mixture is neutralized at low temperature (between 0° and 10° C.) by adding an aqueous solution of an acid such as HCl or H$_2$SO$_4$, and then washed with ethyl acetate.

This gives chlorotrifluoromethylphenols with a degree of conversion of 45% and a yield of 95% (87/13 isomeric distribution of the 2-chloro-4-trifluoromethylphenol and 2-chloro-5-trifluoromethylphenol isomers).

EXAMPLE 2

The procedure of Example 1 is repeated, however, the mixture is heated for 7.5 hours at 83° C. The degree of conversion is 62% and the yield of chlorotrifluoromethylphenol is 87%.

EXAMPLE 3

A mixture of 3,4-dichlorotrifluoromethylbenzene (30 millimols) and KOH (containing 15% of water) (70 millimols), ground in a mechanical mill so as to give a KOH particle size of between 5 and 1,500 microns, is reacted in dimethyl sulphoxide (28 ml) for 8 hours at 85° C. The reaction mixture is stirred, in an inert atmosphere, with a stirrer rotating at 450 rpm.

At the end of the reaction, the reaction medium is treated as in Example 1.

This gives chlorotrifluoromethylphenols with a degree of conversion of 80% and a yield of 85%.

EXAMPLE 4

A mixture of 3,4-dichlorotrifluoromethylbenzene (28 millimols) and powdered KOH (64 millimols), prepared from potassium hydroxide pellets, containing 85% by weight of potassium hydroxide, ground in a mortar so as to give a particle size of less than 1 mm, is reacted in dimethyl sulphoxide (28 ml) for 23 hours at 65° C. The reaction is also carried out in the presence of tris-(3,6-dioxaoctyl)-amine (6 millimols) as a catalyst. The stirring speed is approximately 500 rpm.

This gives chlorotrifluoromethylphenols with a degree of conversion of 63% and a yield of 67%.

EXAMPLE 5

A mixture of 3,4-dichlorotrifluoromethylbenzene (28 millimols) and powdered KOH (64 millimols), identical to that used for Example 4, is reacted in dimethyl sulphoxide (28 ml) for 23 hours at 65° C. The reaction is also carried out in the presence ot tetraoctylammoniua: bromide (6.5 millimols) as a catalyst. The stirring speed is approximately 500 rpm.

This gives chlorotrifluoromethylphenols with a degree of conversion of 53% and a yield of 67%.

EXAMPLE 6

A mixture of 3,4-dichlorotrifluoromethylbenzene (28 millimols) and powdered KOH (54 millimols), is reacted in dimethyl sulphoxide (28 ml) for 76 hours at 66° C. The stirring speed is approximately 500 rpm.

This gives chlorotrifluoromethylphenols with a degree of conversion of 77% and a yield of 71%.

EXAMPLE 6A

By way of comparison, Example 6 was repeated using potassium hydroxide pellets (diameter: 4–5 mm), and the reaction mixture is heated for 64 hours at 65° C. The degree of conversion is 15% and the yield is approximately 30%.

EXAMPLE 7

A mixture of 3,4-dichlorotrifluoromethylbenzene (30 millimols) and powdered NaOH (68 millimols), identical to that used in Example 1, is reacted in dimethylacetamide (28 ml) for 22 hours 30 minutes at 80° C. The stirring speed is 400 rpm.

This gives chlorotrifluoromethylphenols with a degree of conversion of 31% and a yield of 87%.

EXAMPLE 8

A mixture of e,4-dichlorotrifluoromethylbenzene (30 millimols) and powdered NaOH (70 millimols), identical to that used for Example 1, is reacted in N-methylpyrrolidone (28 ml) at 80° C. for 23 hours 30 minutes. The stirring speed is 400 rpm.

This gives chlorotrifluoromethylphenols with a degree of conversion of 37% and a yield of 93%.

What is claimed is:

1. A process for preparing a compound of the formula:

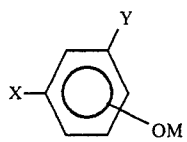

wherein:

X is selected from the group consisting of halogen and trifluoromethyl;

Y is selected from the group consisting of hydrogen, halogen, trifluoromethyl and alkyl having 1 to 4 carbon atoms provided that when Y is halogen, X is trifluoromethyl; and M is selected from the group consisting of hydrogen, alkali metal cation and alkaline earth metal cation;

which comprises reacting in the presence of an aprotic polar solvent, a compound having the formula:

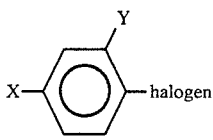

with a powdered basic component selected from the group consisting of alkaline earth and alkali metal hydroxides, and mixtures thereof, said powdered components having a particle size of less than 4 mm; said reaction taking place at a temperature between about 50° C. and about 120° C.

2. A process according to claim 1 wherein the particles of said powdered basic component are less than about 1.5 mm.

3. A process according to claim 1 wherein the particles of said powdered basic component are less than about 0.5 mm.

4. A process according to claim 1 wherein the particles of said powdered basic component are in the range of about 0.005 mm. to about 4 mm.

5. A process according to claim 1 wherein the particles of said powdered basic component are in the range of about 0.005 mm. to about 2 mm.

6. A process according to claim 1 wherein the particles of said powdered basic component are in the range of about 0.005 mm to about 1.5 mm.

7. A process according to claim 1 wherein the temperature at which the reaction takes place is between about 60° and about 90° C.

8. A process according to claim 1 wherein said aprotic polar solvent is selected from the group consisting of hexamethylphosphotriamide, dimethylacetamide, dimethylsulphoxide and N-methylpyrrolidone.

9. A process according to claim 1 wherein said aprotic polar solvent is dimethyl sulphoxide.

10. A process according to claim 1 wherein said aprotic polar solvent has a dielectric constant between about 30 and about 70.

11. A process according to claim 1 wherein the powdered basic component is selected from the group consisting of calcium hydroxide, magnesium hydroxide, sodium hydroxide and potassium hydroxide.

12. A process according to claim 1 wherein the powdered basic component is selected from the group consisting of sodium hydroxide and potassium hydroxide.

13. A process according to claim 1 wherein the starting compound having the formula

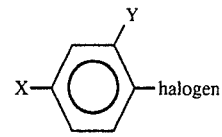

and the powdered basic component are present in the molar ratio 2:3.

14. A process according to claim 1 wherein the reaction is carried out in the presence of a catalyst.

15. A process according to claim 14 wherein the catalyst is selected from the group consisting of substituted quarternary ammonium salts, crown ethers and trispolyoxyalkyl compounds containing from 6 to 40 carbon atoms.

16. A process according to claim 14 wherein said catalyst is used in an amount between about 1% and about 20% of the molar amount of powdered basic component present in the reaciton mixture.

17. A process according to claim 14 wherein the catalyst is selected from the group consisting of monoalkyl ammonium, dialkylammonium and trialkylammonium salts.

18. A process according to claim 1 wherein the starting compound having the formula:

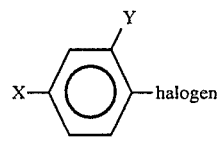

and the powdered basic component are present in the molar ratio of from about 1:1 to about 1:4.

19. A process according to claim 18 wherein said molar ratio is from about 1:2 to about 1:3.

* * * * *